United States Patent [19]

Cox, Jr.

[11] 4,178,643
[45] Dec. 18, 1979

[54] VALVE FOR INFLATABLE PROSTHESIS

[76] Inventor: James E. Cox, Jr., 1257 San Antonio Creek Rd., Santa Barbara, Calif. 93111

[21] Appl. No.: 836,736

[22] Filed: Sep. 26, 1977

[51] Int. Cl.² .............................................. A61F 1/24
[52] U.S. Cl. ........................................ 3/36; 128/274; 128/462; 137/848; 251/149; 251/349
[58] Field of Search ................... 3/36; 128/462, 274; 137/848; 251/149, 349, 353, 354; 46/90; 223/67; 9/314; 141/313

[56] References Cited

U.S. PATENT DOCUMENTS

| | | | |
|---|---|---|---|
| 2,236,293 | 3/1941 | Lund | 137/848 X |
| 2,597,924 | 5/1952 | Davenport, et al. | 128/462 |
| 3,523,563 | 8/1970 | Mirando | 46/90 X |
| 3,566,875 | 3/1971 | Stoehr | 137/848 X |
| 3,845,507 | 11/1974 | Kirby, et al. | 128/462 X |
| 3,852,833 | 12/1974 | Köneke, et al. | 3/36 |

Primary Examiner—Clifford D. Crowder
Attorney, Agent, or Firm—Donald D. Mon

[57] ABSTRACT

A valve for an inflatable prosthesis of the type which comprises a fluid-containing envelope with an aperture closed by a valve through which a desired amount of fluid can be filled or withdrawn. The valve comprises a flat elongated conduit having a pair of sealed edges, and between said edges a pair of flat flexible wall members facing each other to form a fluid seal when they bear against one another. The conduit is open at one end. At the other end it is closed except for a slit formed in one of the walls without removal of material. The valve tends to remain closed both as a consequence of inherent closure of the slit and also as a consequence of pressure of the walls against one another.

8 Claims, 8 Drawing Figures

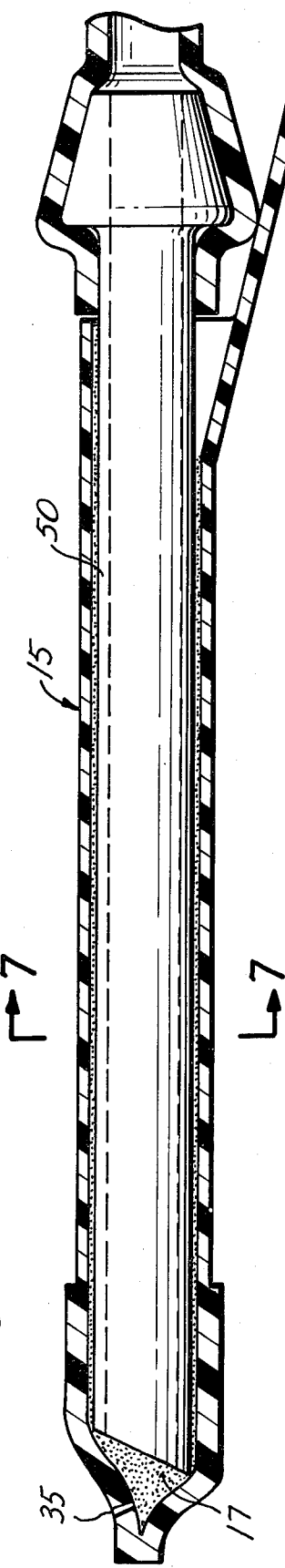
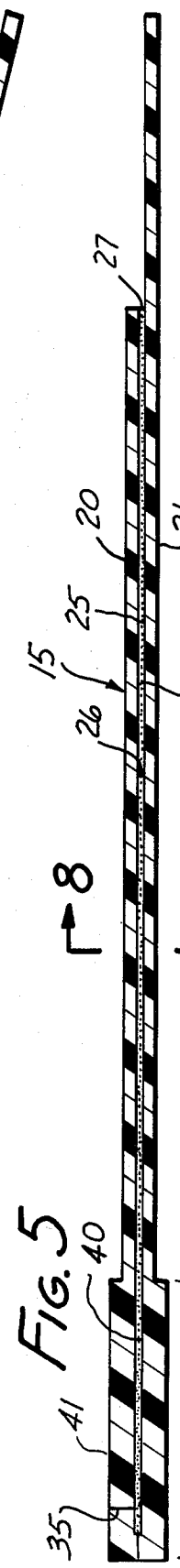
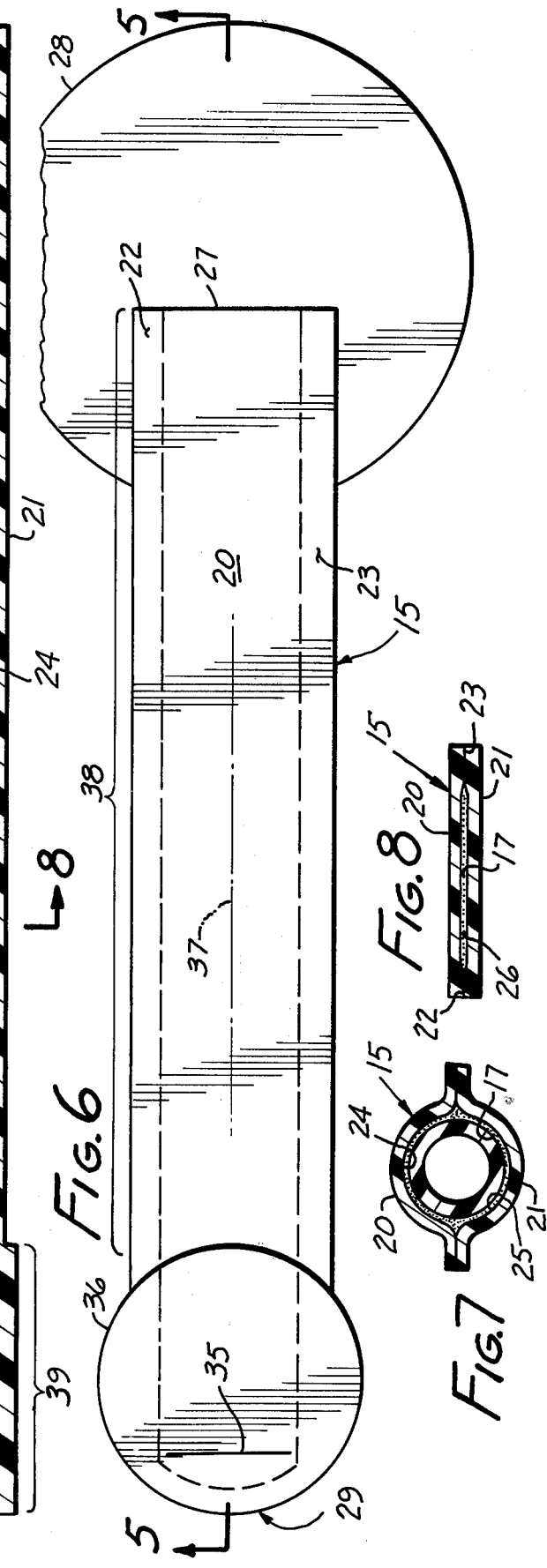
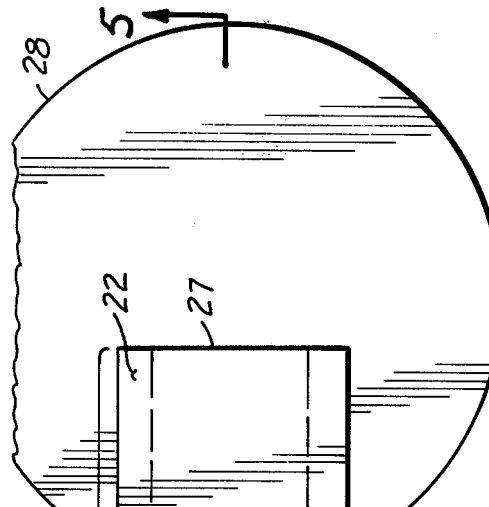
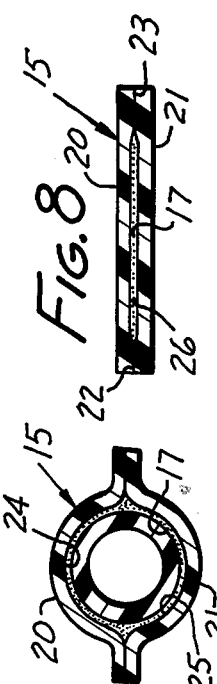

VALVE FOR INFLATABLE PROSTHESIS

This invention relates to valves for inflatable prostheses.

Inflatable prostheses for the human body are well-known. One well-known example is an inflatable mammary prosthesis of the type shown in McGhan U.S. Pat. No. 3,852,832, issued Dec. 10, 1974. Classically such a prosthesis comprises a flexible fluid-containing envelope with an aperture closed by a valve through which a desired amount of fluid can be filled or withdrawn. The term "inflatable" does not mean inflatable in the sense of a distended balloon, but rather a body which, while it can be distended, usually is not. It serves flexibly to encapsulate a volume of fluid in a body cavity. The size of the prosthesis is determined by the amount of fluid contained therein. The term "inflatable" includes not only inflation with gases, but also and more usually total or partial filling with a liquid such as saline solution. Such prostheses are generally made from medical grade silicone rubber which is not deleterious to surrounding human tissue.

A problem with inflatable prostheses is that the valves are either unreliable, complicated, or both. There remains a need for a simple valve which at once is substantially leak-proof and simple. Attempts to make a valve more reliable by going to greater complexity suffer from the fact that if anything goes wrong, it is necessary to make a surgical incision to reach the device in order to repair it. If the valve leaks, an incision must be made to reinflate the prosthesis.

It is an object of this invention to provide a valve for an inflatable prosthesis which is elegantly simple and very reliable.

A valve according to this invention is intended to fit in an aperture in a fluid-containing envelope, and to comprise the only exit or entrance for fluid from and to the inside of the envelope. This valve comprises a flat elongated conduit having a pair of longitudinal, spaced apart sealed edges. The edges are connected by a pair of flat flexible wall members which face each other and can abut one another, whereby to form a fluid seal when they bear against one another. The conduit is open at one end. It is closed at the other end except for a slit formed in one of the walls without removal of material. This valve tends to remain closed both as a consequence of the inherent closure of the material, by return to its relaxed condition, and also as a consequence of pressure of the walls against one another. The conduit is sufficiently flexible to receive a fill tube from the open end to open the slit by mechanically or by differential pressure.

According to a preferred but optional feature of the invention, a quantity of viscous gel is disposed between the walls whereby to improve the sealing properties of the conduit.

According to still another preferred but optional feature of the invention, the slit is formed in one of said walls, and the other of the walls opposite the slit is more rigid adjacent to the slit than the walls significantly far removed from the slit, whereby to form a base against which the wall carrying the slit can bear.

The above and other features of this invention will be fully understood from the following detailed description and the accomanying drawings in which:

FIG. 4 is an enlarged showing of a portion of FIG. 3;

FIG. 5 is a cross-section taken at line 5—5 of FIG. 6;

FIG. 6 is a top view of FIG. 5; and

FIGS. 7 and 8 are cross-sections taken at lines 7—7 and 8—8 in FIGS. 4 and 5, respectively.

Figure 1:
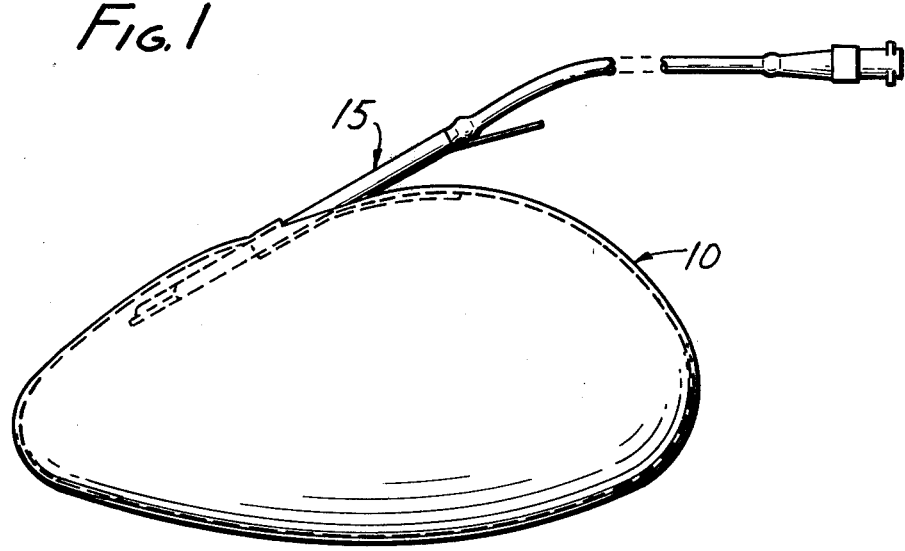
FIG. 1 is a side elevation of a mammary prosthesis including the valve of the invention with a fill tube therein.
Figure 2:
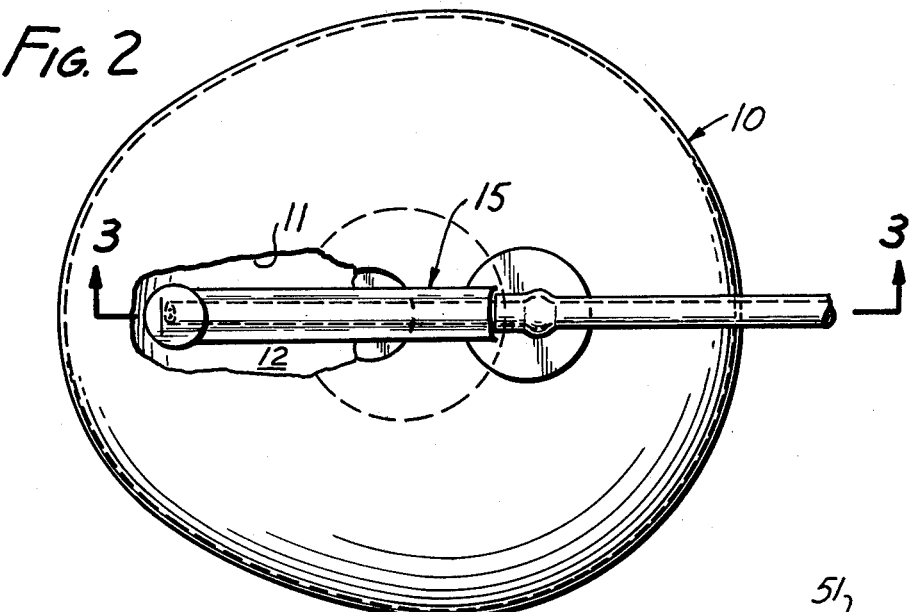
FIG. 2 is a top view of FIG. 3 partly in cutaway section.
Figure 3:
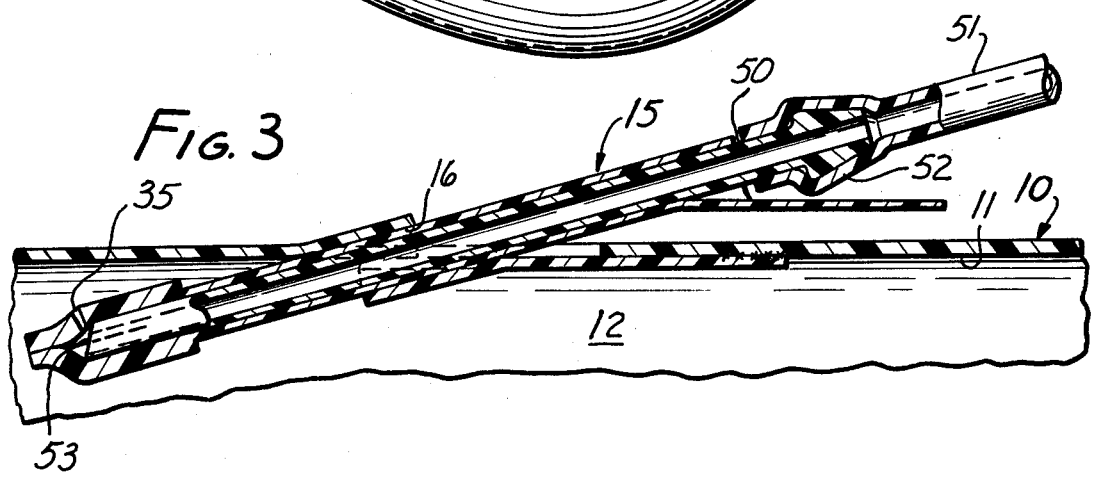
FIG. 3 is a cross-section taken at line 3—3 of FIG. 2.

In FIGS. 1 and 2 there is shown a mammary prosthesis 10 which comprises a fluid-containing flexible envelope 11. This envelope is a continuous hollow structure with a cavity 12 therein. A preferred material for such a device is medical grade silicone rubber because it does not react with the surrounding human tissue. The thickness of the material is on the order of 0.010–0.015 inches whereby the envelope itself is quite pliable. It is inflatable in the sense that its volume is determined by the quantity of the fluid which is placed in it. This does not mean that the mammary prosthesis is intended to be distended by the material and stretched in tension, although it may be, nor does it mean that it must be filled only with a gas for this purpose. Instead it can be filled either with gas or fully or partially with liquid. Filling with liquid is by far the more conventional technique. Saline solution is usually used because if the envelope leaks it does no harm to the body. The function of this prosthesis is to hold this given volume of fluid encapsulated in a cavity in the body such as the inside of a womans breast after removal of the gland. It is evident that prostheses of different shapes can be used for different purposes throughout the body to fill out body contours or to fill regions from which something has been excised.

A valve 15 according to the invention provides the only entrance and exit to the prosthesis. Accordingly, an aperture 16 in the form of a slit is formed in the prosthesis and the valve is cemented therein so as to close the envelope. The slit is preferably normal to the longitudinal axis. The valve itself comprises a conduit 17 formed by a pair of flexible wall members 20, 21 which are flat thin sheets of medical grade silicone rubber or other suitable flexible material. These are joined at their longitudinal sides by longitudinally extending parallel sealed edges 22, 23.

These may be formed by cementing, heat sealing, or any other suitable technique. Between the sealed edges there are faces 24, 25 which face one another and which are not sealed to one another and which thereby can form the conduit. These faces are preferably in substantial contiguous abutment, although they may be spaced apart from one another by a small spacing.

In the various figures and especially in FIGS. 5 and 8 there is shown a layer 26 of a viscous gel, for example a silicone rubber gel of medical grade silicone, whose thickness is greatly exaggerated for purposes of illustration. Actually its thickness is so small as to cause no substantial deflection of the walls and this is indicated in FIG. 8 wherein the outside surfaces of the walls are straight lines while the inside is shown as distended. This of course is an impossibility because any distension on the inside will be reflected on the outside, but it is intended that the gel not be substantially thicker than a relatively thick film so that it will tend to remain in place and not be squeezed out. In any event it does tend to make a better fluid sealing contact between faces 24 and 25 when they are pressed together. In this specification and in the claims, faces 24 and 25 are defined as facing each other, being able to be brought into contact with one another. This terminology is intended to include being brought together against one another with layer 26 between them.

The conduit is open at end 27, which is a non-adherent edge of the two sheets. If desired a tab 28 may form a continuation of wall 21 to facilitate handling. At the other end 29 of the valve the conduit is closed except for a slit 35. This slit is formed by a plunge cut through wall member 20 without removal of material. Under these circumstances, return of the material to its relaxed condition will cause closure of the slit. This other end is preferably formed as a disc 36 wherein the two wall members are peripherally joined around the edge of the disc and the slit extends transversely relative to central axis 37. In this region, both wall members 20 and 21 are relatively thicker than they are at a substantial distance from the slit i.e., in the region 38 where sealing occurs in the conduit itself. The thicker portion 39 of wall member 21 therefore forms a base with an upper surface 40 against which the flexible slitted portion 41 can bear. This aids in defining the closed position. Both the base and the slitted portion may be made relatively stiff, but of course portion 41 must be flexible and the less flexible portion 39 is, then the more stretchable must be portion 41. A useful technique is to make slitted portion 41 somewhat thinner than the base portion, although equality of thickness may be used as shown in FIG. 5.

A fill tube 50 comprises an extended tubing 51 with a coupling 52 at one end and an opening 53 at the other end. To fill or to drain the prosthesis, the fill tube is inserted into the conduit to the region where the slit is so as to distend the slit by deforming the structure as shown in FIG. 4. Under these circumstances, the slit will be held open and fluid can pass in either direction. If it were desired to inject fluid into the prosthesis and not drain it, then of course the differential pressure alone would cause the conduit and the slit to open.

When the desired amount of fluid is injected into the prosthesis, the fill tube is withdrawn and the valve will progressively close, first closing the slit as soon as the fill tube is withdrawn from the base, and then gradually closing the conduit by contact of the two faces against one another. On the outside of the prosthesis, the fingers of the surgeon can press the two faces together which, even without the gel, will cause close fluid sealing contact because of the atmospheric or other pressure against it. When the gel is present it makes an even more positive seal.

It will be seen that although the conduit can be formed from a flattened tubing, a more reliable fluid seal will be obtained by building the valve from two flat pieces of material and cementing them together at the edges as shown.

This invention is not to be limited by the embodiment shown in the drawings and described in the description, which is given by way of example and not of limitation, but only in accordance with the scope of the appended claims.

I claim:

1. A valve for an inflatable prosthesis of the type which comprises a fluid-containing envelope with an aperture closed by a valve through which a desired amount of fluid can be filled or withdrawn, said valve comprising: a flat elongated conduit having a pair of sealed edges, and between said edges a pair of flat flexible wall members facing each other to form a fluid seal when they bear against one another, the conduit being open at one end, and at the other end closed but for a slit formed in one of said wall members without removal of material whereby to have a pair of contiguous slit edges when the slit is closed, said slit being spaced from both of said ends and edges, and thereby being totally surrounded by the material of its respective wall member so that both of said edges are distensible, whereby said valve tends to remain closed both as a consequence of inherent closure of said slit, and also as a consequence of pressure of said walls against one another, said conduit being sufficiently flexible to receive a fill-tube in said open end, said fill tube when inserted separating the wall members from one another, and when fully inserted holding the slit open; and a layer of viscous gel disposed between said wall members, whereby to improve the sealing properties of the conduit, said layer being non-adhesive and so thin that pressure against the walls does not substantially extrude the gel from the conduit.

2. A valve according to claim 1 in which the said slit is formed in one of said wall members, and in which the other of said wall members is more rigid adjacent to the slit that it is at its wall removed from the slit, whereby to form a base against which the wall carrying the slit can bear.

3. A valve according to claim 2 in which the said base is disc shaped.

4. A valve according to claim 1 in which said walls are so constructed and arranged that, prior to insertion of the gel between them, they lay in face-to-face contiguity.

5. A valve according to claim 1 in which the slit lies normal to the longitudinal axis of the conduit.

6. In combination: an inflatable prosthesis comprising an envelope having a fluid impermeable outside boundary with an aperture therethrough; and a valve mounted to said envelope in said aperture so as to control flow of fluid into and out of said envelope, said valve comprising: a flat enlongated conduit having a pair of sealed edges, and between said edges a pair of flat flexible wall members facing each other to form a fluid seal when they bear against one another, the conduit being open at one end, and at the other end closed but for a slit formed in one of said wall members without removal of material whereby to have a pair of contiguous slit edges when the slit is closed, said slit being spaced from both of said ends and edges, and thereby being totally surrounded by the material of its respective wall member so that both of said edges are distensible, whereby said valve tends to remain closed both as a consequence of inherent closure of said slit, and also as a consequence of pressure of said walls against one another, said conduit being sufficiently flexible to receive a fill-tube in said open end, said fill tube when inserted separating the wall members from one another, and when fully inserted holding the slit open; and a layer of viscous gel disposed between said wall members, whereby to improve the sealing properties of the conduit, said layer being non-adhesive and so thin that pressure against the walls does not substantially extrude the gel from the conduit, said wall members projecting beyond said outside boundary of said prosthesis whereby to be available for pressing by the hands of the surgeon to press the wall members together.

7. A combination according to claim 6 in which said slit is formed in one of said wall members, and in which the other of said wall members is more rigid adjacent to the slit than it is at its wall removed from the slit, whereby to form a base against which the wall member carrying the slit can bear.

8. A combination according to claim 7 in which said base is spaced from, inside of, and connected to said prosthesis only through said wall members.

* * * * *